US012729220B2

(12) United States Patent
Gagnon

(10) Patent No.: US 12,729,220 B2
(45) Date of Patent: Sep. 8, 2026

(54) PURIFICATION PROCESS FOR LIPID-MEMBRANE-ENCLOSED COMPLEX ASSEMBLAGES

(71) Applicant: Sartorius BIA Separations d.o.o., Ajdovscina (SI)

(72) Inventor: Peter S. Gagnon, Las Vegas, NV (US)

(73) Assignee: SARTORIUS BIA SEPARATIONS, Ajdovscina (SI)

( * ) Notice: Subject to any disclaimer, the term of this patent is extended or adjusted under 35 U.S.C. 154(b) by 539 days.

(21) Appl. No.: 18/035,005

(22) PCT Filed: Nov. 3, 2021

(86) PCT No.: PCT/EP2021/080501
§ 371 (c)(1),
(2) Date: May 2, 2023

(87) PCT Pub. No.: WO2022/096499
PCT Pub. Date: May 12, 2022

(65) Prior Publication Data
US 2023/0391822 A1 Dec. 7, 2023

(30) Foreign Application Priority Data
Nov. 4, 2020 (EP) .................................... 20205655

(51) Int. Cl.
*C07K 1/22* (2006.01)
*B01D 15/20* (2006.01)
(Continued)

(52) U.S. Cl.
CPC .............. *C07K 1/22* (2013.01); *B01D 15/203* (2013.01); *B01D 15/3828* (2013.01); *C12N 5/00* (2013.01)

(58) Field of Classification Search
None
See application file for complete search history.

(56) References Cited

U.S. PATENT DOCUMENTS

2015/0010951 A1* 1/2015 LaPointe .............. C12Q 1/6806
536/25.4
2016/0266097 A1* 9/2016 Gagnon ............... B01D 15/364

FOREIGN PATENT DOCUMENTS

CN 110551687 A 12/2019
EP 3569695 A1 11/2019
(Continued)

OTHER PUBLICATIONS

Li et al. (Fe(III)-based immobilized metal-affinity chromatography (IMAC) method for the separation of the catechol siderophore from Bacillus tequilensis CD36. 3 Biotech. Sep. 2018;8(9):392. (Year: 2018).*

(Continued)

*Primary Examiner* — Thomas J. Visone
*Assistant Examiner* — Georgiana C Reglas
(74) *Attorney, Agent, or Firm* — Christensen, Fonder, Dardi, Busse; Diane E. Bennett; Peter S. Dardi

(57) ABSTRACT

A chromatographic method for separation of lipid-membrane-enclosed compound assemblages (LMCAs) from chromatin heteroaggregates including degraded remnants from LMCAs in a sample,
contacting the sample with a chromatographic material with a surface having cationic metal affinity ligands said chromatographic material being charged with ferric iron, manganese, calcium, or magnesium ions, and being equilibrated with an equilibration buffer,
applying a gradient of a first elution buffer comprising a non-metal-chelating salt, thereby
eluting LMCAs.

19 Claims, 1 Drawing Sheet

(51) Int. Cl.
*B01D 15/38* (2006.01)
*C12N 5/00* (2006.01)

(56) References Cited

FOREIGN PATENT DOCUMENTS

| | | |
|---|---|---|
| JP | 2020-505061 A | 2/2020 |
| WO | 2014-123484 A1 | 8/2014 |
| WO | 2014-133459 A1 | 9/2014 |
| WO | 2019-122003 A1 | 6/2019 |
| WO | 2020-120801 A1 | 6/2020 |
| WO | 2020-127505 A1 | 6/2020 |

OTHER PUBLICATIONS

Corso et al. Reproducible and scalable purification of extracellular vesicles using combined bind-elute and size exclusion chromatography. Sci Rep 7, 11561 (2017) (Year: 2017).* chromforum.org users "carlo.annaratone" and "Markus Laeubli" ("EDTA as mobile phase for HPLC" discussion forum; May 2015; retrieved from https://www.chromforum.org/viewtopic.php?t=26780 on Aug. 13, 2025) (Year: 2015).*

Vrabec et al. Emerging tools for exosome purification and in-process monitoring, Bioprocess International eBook, Mar. 22, 2019, https://bioprocessintl.com/analytical/downstream-validation/emerging-tools-for-exosome-purification-and-in-process-monitoring (Year: 2019).*

Chen et al., "Histone-dependent IgG Conservation in Octanoic Acid Precipitation and its Mechanism", Applied Microbiology and Biotechnology, vol. 100 No. 23, p. 9933-9941, (Jul. 14, 2016).

Ribeiro et al., "Effect of IDA and TREN Chelating Agents and Buffer Systems on the Purification of Human IgG with Immobilized Nickel Affinity Membranes" Journal of Chromatography B, vol. 861 No 1, p. 64-73, (Nov. 23, 2007).

International Search Report for corresponding Patent Application No. PCT/EP2021/080501 dated Feb. 7, 2022.

Office Action from corresponding Japanese Patent Application No. 2023-527650 dated Sep. 30, 2025.

* cited by examiner

PURIFICATION PROCESS FOR LIPID-MEMBRANE-ENCLOSED COMPLEX ASSEMBLAGES

CROSS REFERENCE TO RELATED APPLICATIONS

This application is a National Stage filing of PCT Application No. PCT/EP2021/080501 filed Nov. 3, 2021, entitled "Purification Process For Lipid-Membrane-Enclosed Complex Assemblages", which claims priority to European Patent Application No. 20205655.2, filed Nov. 4, 2020.

The invention pertains to a chromatographic method for separation of lipid-membrane-enclosed compound assemblages (LMCAs) from chromatin heteroaggregates that include degraded remnants from LMCAs in a sample.

BACKGROUND

The term "complex assemblage" is used in the field of biology to refer to a structurally organized entity that contains more than one species of biomolecules and which typically contains biomolecules from more than one class, such as proteins, carbohydrates, and nucleic acids, among others. Some complex assemblages are enclosed by lipid-membranes, such as cellular vesicles, extra-cellular vesicles, and lipid-enveloped viruses. The majority exist in a range of sizes from about 30 nm to about 300 nm, with some up to 10 or more times larger.

Recent experimental work demonstrates that unpurified preparations of lipid-membrane-enclosed compound assemblages (LMCAs) are accompanied by a particular class of contaminants comprising their degraded remnants [1,2]. They are detected by immunological staining of protein markers specific for a particular LMCA. Size exclusion chromatography suggests that the majority of such remnants range in size from about 2 nm to about 50 nm.

Chromatin represents a known class of contaminants in cell culture harvests. It consists of degraded nucleosomal arrays containing host cell DNA and histone proteins [3]. It is often bound secondarily to RNA and other proteins, creating heteroaggregates, where the term heteroaggregate is understood to refer to an un-organized complex of more than one class of biochemical species. Chromatin heteroaggregates remaining in cell culture harvests are known to exist in a range of 2 nm to more than 5 microns. Filtration with a 0.45 micron membrane reduces the upper end of the range to about 400 nm.

Recent experimental data show that a particular subset of chromatin heteroaggregates includes degraded remnants of LMCAs [4]. This extended class of chromatin heteroaggregates is defined by its inclusion of LMCA membrane protein markers characteristic of a given species of compound assemblage, combined with an excess of surface-accessible nucleic acids from their chromatin component. Surface accessibility of excess nucleic acids is a key defining characteristic of these heteroaggregates. Many species of LMCAs include nucleic acids but the nucleic acids are enclosed within the lipid membrane so long as the LMCAs remain intact. Chromatin heteroaggregates that include LMCA remnants exist in sizes ranging from less than 100 nm to more than 1000 nm [4].

Chromatin heteroaggregates that include LMCA remnants cause problems particular to production of LMCAs for therapeutic applications. Such heteroaggregates cause immunological assays to inflate the apparent content of intact LMCAs. This is also a problem for affinity chromatography methods that recognize LMCAs by their membrane proteins since chromatin heteroaggregates that include those proteins will also be captured. The size overlap of LMCAs and chromatin heteroaggregates that contain LMCA remnants also renders size-based purification methods unable to separate them.

Anion exchange chromatography has some potential to separate LMCAs from chromatin heteroaggregates that include LMCA remnants but its utility is restricted to heteroaggregates with exteriors that are highly dominated by nucleic acid residues (1-3). Such heteroaggregates typically do not elute in sodium chloride but intact LMCAs do. Chromatin heteroaggregates that include LMCA remnants with lesser amounts of nucleic acids on their surfaces co-elute with intact LMCAs [4] (FIG. 1). This represents an important issue for therapeutic applications of LCMAs since regulatory agencies worldwide consistently require that contaminating DNA be reduced to extremely low levels.

LMCAs sometimes present the additional purification challenge of separating LMCAs that are deficient with respect to phosphatidylserine in their outer membrane leaflets from LMCAs that contain an excess of phosphatidylserine in their outer membrane leaflets. Excess phosphatidylserine in the outer membrane leaflets is an indicator that the source cell of a particular LMCA was inflamed, infected, diseased, dying, or dead [5]. No chromatography method is known at present that can fractionate LCMAs with phosphatidylserine on their outer membrane surfaces from LCMAs that lack phosphatidylserine on their outer membrane surfaces.

SUMMARY OF THE INVENTION

The invention pertains to a chromatographic method for separation of lipid-membrane-enclosed compound assemblages (LMCAs) from chromatin heteroaggregates including degraded remnants from LMCAs in a sample comprising the steps of:

- contacting the sample with a chromatographic material with a surface having cationic metal affinity ligands said chromatographic material being charged with ferric iron, manganese, calcium, or magnesium ions, and being equilibrated with an equilibration buffer,
- applying a gradient of a first elution buffer comprising a non-metal-chelating salt, thereby
- eluting LMCAs.

In an embodiment of the method of the invention the LMCA can be selected from the group consisting of a cellular vesicle, an extra-cellular vesicle, a non-cellular vesicle, a cellular organelle, an exosome, a small extra-cellular vesicle, a microvesicle, a medium extra-cellular vesicle, a ribosome, a mitochondrion, a lipid-enveloped virus or lipid-enveloped virus-like particle, an influenza virus, a corona virus, a lentivirus, a cytomegalovirus, a liposome and combinations thereof.

In another embodiment of the method of the invention the non-metal-chelating salt is a monovalent halide salt, in particular sodium chloride.

In still another embodiment of the method of the invention the sample can be a cell culture harvest, a filtered cell culture harvest, a concentrated filtered cell culture harvest, a partially purified preparation containing a LMCA and chromatin heteroaggregates including LMCA remnants. In yet another embodiment of the method of the invention chromatin heteroaggregates that include degraded remnants from LMCAs can be eluted in a gradient of a second eluting buffer comprising a chelating salt.

In a further embodiment of the method of the invention the chelating salt of the second eluting buffer can be selected from the group consisting of a metal phosphate salt, or a metal citrate salt, or a metal salt of ethylenediaminetetraacetic acid (EDTA), or a metal salt of ethylene glycol-bis ((3-aminoethyl ether)-N,N,N',N'-tetraacetic acid, also known as egtazic acid (EGTA), and combinations thereof.

In a still further embodiment of the method of the invention the method may be combined with at least one additional method for reduction of chromatin heteroaggregate content.

In further embodiment of the method of the invention the at least one additional method can be a treatment with nuclease enzymes and/or treatment with a solid phase bearing an anionic chromatography ligand.

In another embodiment of the method of the invention the solid phase bearing an anionic chromatography ligand can be charged with iron or manganese ions.

In still another embodiment of the method of the invention the sample is contacted with the chromatographic material and after an incubating time separated from the chromatographic material.

In yet another embodiment of the method of the invention the sample, in particular a cell culture harvest containing exosomes can be diafiltered by tangential flow filtration.

In another embodiment of the method of the invention the cationic metal affinity ligand may be tris(2-aminoethyl) amine (TREN).

In a further embodiment of the method of the invention the equilibration buffer may comprise a pH value in the range of pH 5 to pH 9, or pH 6 to pH 8, or preferably pH 6.5 to pH 7.5, and a conductivity value of 1 mS/cm to 250 mS/cm, or 2 mS/cm to 100 mS/cm, or 3 mS/cm to 50 mS/cm, or 4 mS/cm to 20 mS/cm, or preferably 5 mS/cm to 10 mS/cm.

The invention is a chromatographic method for separation of intact lipid-membrane-enclosed compound assemblages (LMCAs) from chromatin heteroaggregates that include degraded remnants from LMCAs. It has been surprisingly discovered that a cationic metal affinity ligand preferably bearing ferric iron or manganese ions elutes intact LMCAs in a gradient with a non-metal-chelating salt such as sodium chloride. Chromatin heteroaggregates that include degraded remnants from LMCAs are more strongly retained. Some can be eluted in a gradient with a chelating salt such as sodium phosphate. The remainder can be eluted with sodium hydroxide. An extended variant of the invention combines the basic invention with one or more additional methods for reduction of chromatin heteroaggregate content such as treatment with nuclease enzymes and/or treatment with a solid phase bearing an anionic chromatography ligand preferably charged with iron or manganese ions.

Elements of the invention are illustrated in the following non-limiting embodiments: In one example illustrating the central method, a cationic metal affinity chromatography column is charged with ferric iron then equilibrated to roughly physiological conditions. A filtered cell culture harvest containing exosomes (LMCAs) is applied to the equilibrated cationic metal affinity column, then the column is washed with equilibration buffer. Intact exosomes are eluted with sodium chloride gradient. In an optional extension to the method, chromatin heteroaggregates including LMCA remnants are eluted with a sodium phosphate gradient. The column is cleaned with NaOH.

In one example illustrating a further-extended variant of the method, an anionic metal affinity solid phase is charged with ferric iron then equilibrated to roughly physiological conditions. A cell culture harvest containing exosomes is contacted with the solid phase, incubated for 1 hour, then separated from the solid phase. A major chromatin subset, including chromatin heteroaggregates that are associated with degraded remnants of LMCAs, remain bound to the anionic metal affinity solid phase charged with ferric iron and are thus removed. The treated harvest is then processed by the central method of the invention.

In another example illustrating an extended variant of the method, a cell culture harvest containing exosomes is diafiltered by tangential flow filtration to conditions that are optimal for a nuclease enzyme. The membrane pore size is the largest that will retain the desired LMCAs so that smaller contaminants may be eliminated through the pores. The diafiltered harvest is then treated with nuclease enzyme. Tangential flow filtration is re-commenced to remove nucleotides liberated by the action of the nuclease treatment, along with histones liberated by lysis of the DNA. The exosome-containing retentate may be concentrated if desired. The treated harvest is then processed by the central method of the invention.

In an example illustrating a compound extended variant of the method, an anionic metal affinity solid phase is charged with ferric iron then equilibrated to roughly physiological conditions. A cell culture harvest containing exosomes is contacted with the solid phase, incubated for 1 hour, then separated from the solid phase. A major chromatin subset, including chromatin heteroaggregates that are associated with degraded remnants of LMCAs, remain bound to the anionic metal affinity solid phase charged with ferric iron and are thus removed. Their removal facilitates filterability of the treated harvest. The treated harvest is concentrated and diafiltered by tangential flow filtration to conditions that are optimal for a nuclease enzyme. The membrane pore size is the largest that will retain the desired LMCAs so that smaller contaminants may be eliminated through the pores. The diafiltered harvest is then treated with nuclease enzyme. Tangential flow filtration is re-commenced to remove nucleotides liberated by the action of the nuclease treatment, along with histones liberated by lysis of the DNA. The exosome-containing retentate may be concentrated if desired. The treated harvest is then processed by the central method of the invention.

DETAILED DESCRIPTION OF THE INVENTION

Figure 1:
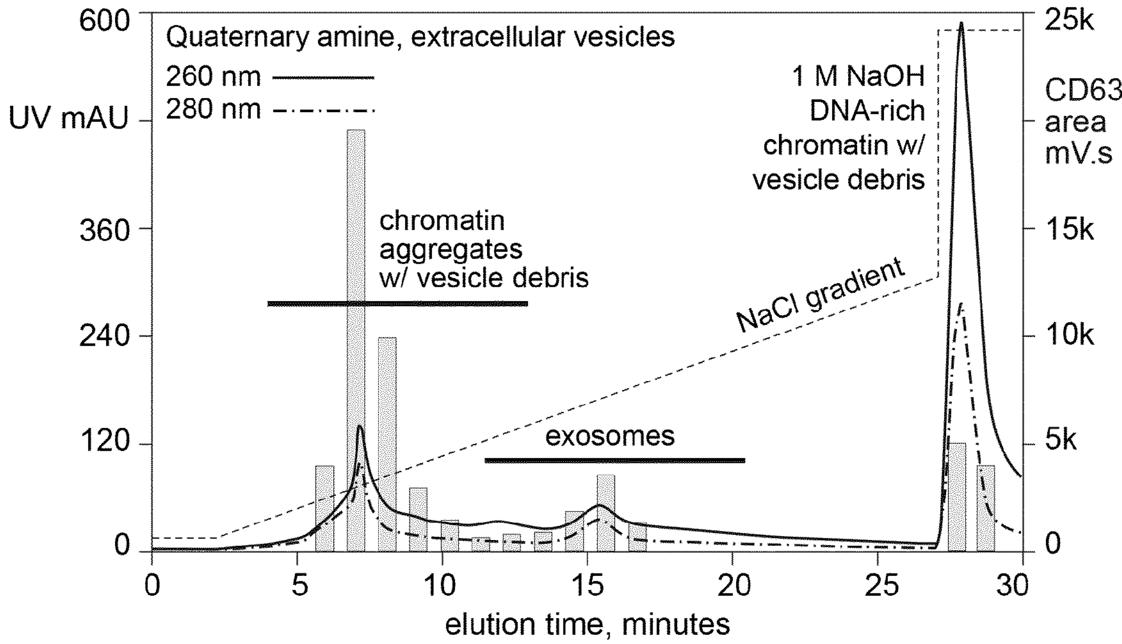
FIG. 1 depicts the elution of exosomes and exosome fragment-chromatin hybrids from an anion exchange chromatography column.

In one embodiment, a LMCA species to be processed by the method of the invention includes a cellular vesicle, or an extra-cellular vesicle, or a non-cellular vesicle or a cellular organelle. In one such embodiment, a LMCA species to be processed by the method of the invention includes an exosome, or a small extra-cellular vesicle, or a microvesicle, or a medium extra-cellular vesicle, or a ribosome, or a mitochondrion. In another embodiment, a LMCA species to be processed by the method of the invention includes a lipid-enveloped virus or lipid-enveloped virus-like particle. In one such embodiment, a LMCA species to be processed by the method of the invention includes an influenza virus, or a corona virus, or a lentivirus, or a cytomegalovirus, or another lipid enveloped virus.

In one embodiment, a sample containing a LMCA species to be processed by the method of the invention is a filtered cell culture harvest, or a concentrated filtered cell culture harvest, or a partially purified preparation containing a desired LMCA species and chromatin heteroaggregates that include LMCA remnants. In one embodiment, the sample is a cell culture harvest that has been treated to reduce the content of nucleic acids. In one embodiment where a sample has been treated to reduce the content of nucleic acids, the method used to reduce nucleic acid content may be treatment with nuclease enzymes. In one embodiment where a sample has been treated to reduce the content of nucleic acids, the method used to reduce nucleic acid content may be treatment with an anionic metal affinity solid phase charged with a metal ion. In one such embodiment, the anionic metal affinity ligand is iminodiacetic acid (IDA). In another such embodiment, the anionic metal affinity ligand is nitrilotriacetic acid (NTA). In one such embodiment, the metal ion used to charge the anionic metal affinity ligand is preferably ferric iron or manganese. In one such embodiment, the solid phase on which the anion metal affinity ligand is covalently attached is a particle, or a fiber, or a membrane, or a monolith, or another configuration, or a mixed configuration, any of which may be packed in a chromatography device, including a chromatography column.

In one embodiment, a cationic metal affinity ligand covalently attached to a solid phase, column, or column packing is tris(2-aminoethyl)amine (TREN).

In one embodiment, a cationic metal affinity ligand is charged with a divalent or trivalent metal ion, such as calcium, magnesium, manganese, or preferably ferric iron.

In one embodiment, a metal-ion-charged cationic metal affinity solid phase is equilibrated to a pH value in the range of pH 5 to pH 9, or pH 6 to pH 8, or preferably pH 6.5 to pH 7.5, and a conductivity value of 1 mS/cm to 250 mS/cm, or 2 mS/cm to 100 mS/cm, or 3 mS/cm to 50 mS/cm, or 4 mS/cm to 20 mS/cm, or preferably 5 mS/cm to 10 mS/cm. It will be evident to persons of knowledge in the art that the preference for near-physiological conditions is intended in part to maintain the stability of the desired LMCA. The chemical selectivity of the method of the invention, independent of the issue of LMCA stability, is maintained over a wider range of pH and conductivity.

In one embodiment, a species of LMCA is eluted from the column by flowing a non-metal-chelating salt containing eluting buffer over the column, where the salt is a monovalent metal halide such sodium chloride, or potassium chloride, or another monovalent metal halide, or sodium acetate or another monovalent metal acetate, or another non-chelating salt, preferably sodium chloride. In one such embodiment, the concentration of sodium chloride is at a concentration in the range of 0.5 M to 2.0 M, or 0.75 M to 1.5 M, or 1.0 M to 1.25 M, or 0.8 M to 1.2 M, or 0.9 M to 1.1 M. In another such embodiment, the concentration of sodium chloride is increased continuously or in steps to a final concentration in the range of 0.5 M to 2.0 M, or 0.75 M to 1.5 M, or 1.0 M to 1.25 M, or 0.8 M to 1.2 M, or 0.9 M to 1.1 M. In any of these embodiments, the operating pH may be the same as equilibration buffer, preferably in the range of 6.5 to 7.5.

In one embodiment, chromatin heteroaggregates that contain remnants of LMCAs are eluted in a separate step after elution of the LMCA. In one such embodiment, chromatin heteroaggregates that contain remnants of LMCAs are eluted with a salt that has the ability to chelate metals. In one such embodiment, chromatin heteroaggregates that contain remnants of LMCAs are eluted with a gradient to 500 mM sodium phosphate, or to 1 M potassium phosphate, or another monovalent metal phosphate salt, or a monovalent metal citrate salt, or a monovalent metal salt of ethylenediaminetetraacetic acid (EDTA), or a monovalent metal salt of ethylene glycol-bis((3-aminoethyl ether)-N,N,N',N'-tetraacetic acid, also known as egtazic acid (EGTA), or a combination thereof. In some such embodiments a chelating salt may be mixed with a non-chelating salt such as a monovalent metal halide salt or a metal acetate salt.

In one embodiment, the metal-charged cationic metal affinity column of the invention may be eluted in a single operation with a step or a gradient to a phosphate, citrate, EDTA, EGTA, or a combination thereof without a prior elution step with a monovalent metal halide, or monovalent metal acetate salt, or other non-chelating salt.

In one embodiment, elution of a species of LMCA may be performed with a step to a sufficiently high concentration of a non-chelating salt to elute the majority of intact LCMAs and concentrate them in a single fraction. In another embodiment, elution of a species of LMCA may be performed in a series of steps in which the final step contains a sufficiently high concentration of a non-chelating salt to elute the majority of intact LMCA and the intermediate steps contain a succession of increasing salt concentration for the purpose of separating the desired intact species of LMCA from contaminants. In another embodiment, elution of a species of LMCA may be performed in a so-called linear gradient whereby the concentration of a non-chelating salt is increased continuously to an endpoint concentration sufficient to elute the majority of intact LMCA.

In one embodiment, the elution of chromatin heteroaggregates may be performed by increasing the concentration of a chelating salt in a single step, in a series of steps, or in a linear gradient to an endpoint of sufficient salt concentration to elute the species of interest.

In one embodiment the method of the invention is used to fractionate extracellular vesicles. In one such embodiment, the method of the invention is used to purify exosomes. In one such embodiment, intact exosomes elute from a ferric-iron loaded cationic metal affinity column such as a TREN column in the presence of chloride ions. In one such embodiment, chromatin heteroaggregates including remnants of exosomes and/or other species of extracellular vesicles elute in the presence of phosphate ions. In another embodiment involving fractionation of extracellular vesicles, the method of the invention is used to fractionate extracellular vesicles, including exosomes, that are deficient phosphatidyl serine in their outer membrane leaflets from extracellular vesicles, including exosomes, that contain excess phosphatidyl serine in their outer membrane leaflets. In one such embodiment, the extracellular vesicles that are deficient in phosphatidyl serine in their outer membrane leaflets elute in sodium chloride while the extracellular vesicles that contain an excess of phosphatidyl serine in their outlets are eluted in sodium phosphate. In one such embodiment, the method of the invention is used to selectively concentrate phosphatidylserine-positive exosomes for the purpose of enhancing the sensitivity and accuracy of a diagnostic test for the presence of phosphatidylserine-positive exosomes.

In one embodiment, the method of the invention is used to fractionate a desired lipid enveloped virus from chromatin heteroaggregates that include degraded remnants of lipid-enveloped virus as well as from degraded remnants from extracellular vesicles.

In one embodiment, a LMCA processed by the method of the invention may be processed further to reduce levels of any contaminant classes that remain. Follow-on method for the purpose may include filtration methods, precipitation methods, and chromatography methods. In one embodiment, where a follow-on purification method is a chromatography method, the chromatography method may be size exclusion chromatography, or anion exchange chromatography, or another chromatography method.

It will be understood by persons of knowledge in the art that ferric-iron loaded cationic metal affinity column of the invention will have a high affinity for endotoxins, due to the positive charge on the column and the high affinity of ferric iron for phosphate residues. It may accordingly be expected that LMCAs eluted in a non-chelating salt will be highly deficient in endotoxins relative to the endotoxin level in the original sample.

EXAMPLES

Example 1

Fractionation of Extracellular Vesicles by the Method of the Invention

Figure 2:
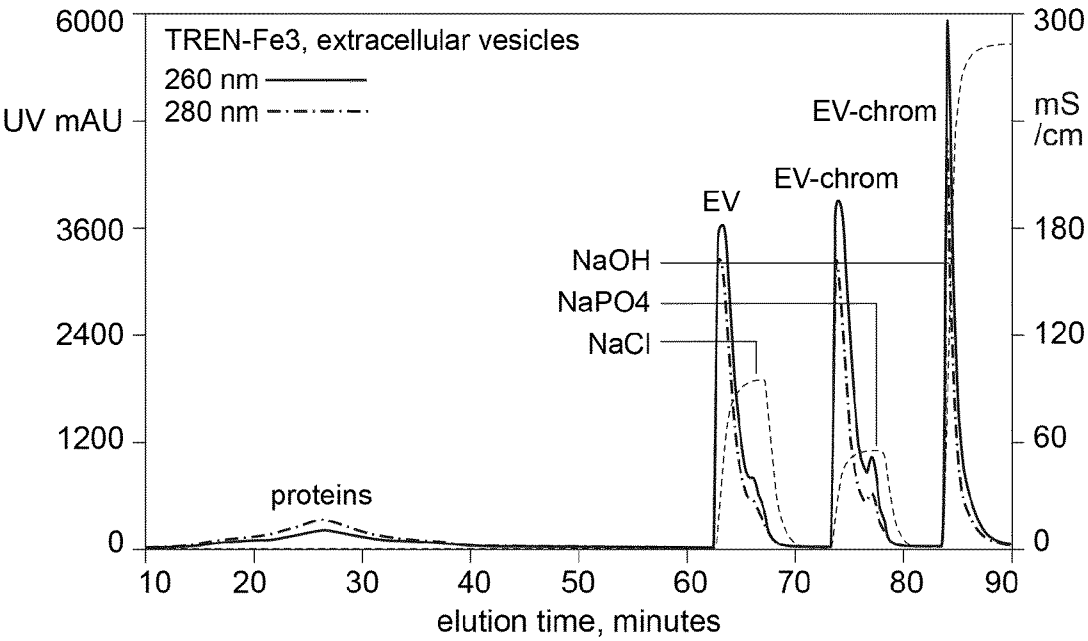
FIG. 2 depicts the elution of exosomes and fragment-chromatin contaminants from a cationic metal affinity chromatography column charged with ferric iron, where the exosomes elute in a sodium chloride gradient while exosome fragment-chromatin contaminants elute in a phosphate gradient or later in sodium hydroxide.

A cationic metal affinity monolith (TREN) was loaded with ferric iron, then equilibrated with 15 column volumes (CV) of 50 mM Hepes, 20 mM NaCl, pH 7.0. Filtered mammalian cell culture harvest containing a mixture of exosomes (small extracellular vesicles (LMCAs)), chromatin, and heteroaggregates including chromatin and degraded vesicular elements was loaded onto the column. Unbound sample components were rinsed off the column with equilibration buffer and the column was eluted by a step to 1.0 M sodium chloride (50 mM Hepes, pH 7.0), continuing for 5 CV. The column was re-equilibrated with the original equilibration buffer, after which a second elution step was applied ending at 500 mM sodium phosphate, pH 7.0, and continuing for 5 CV with 500 mM phosphate. The column was restored to original equilibration conditions then cleaned with 30 CV 1 M NaOH plus 2 M NaCl. The chromatogram is illustrated in FIG. 2. One population of extracellular vesicles eluted in NaCl. A second peak eluted in phosphate despite the phosphate elution having lower conductivity than the chloride elution. This highlights that the phosphate elution selects a different population of extracellular vesicles which sodium chloride was unable to remove. The elution pattern is distinct from anion exchange chromatography (anion exchange chromatography on a quaternary amine is shown in FIG. 1).

Example 2

Fractionation of a Desired Exosome Population (LCMA) from Chromatin Heteroaggregates Including Degraded Remnants from LMCAs A cationic metal affinity monolith (TREN) is loaded with ferric iron, then equilibrated with CV of 50 mM Tris, 20 mM NaCl, pH 7.5. Filtered mammalian cell culture harvest containing a mixture of exosomes, chromatin, and heteroaggregates including chromatin and degraded vesicular elements is loaded onto the column. Unbound sample components are rinsed from the column with equilibration buffer and the column is eluted by a 20 CV linear gradient to 50 mM Tris, 1.0 M sodium chloride, pH 7.0, then continuing under those conditions for 5 CV. The column is then cleaned with 1 M NaOH plus 2 M NaCl.

Example 3

Fractionation of a Phosphatidylserine-Positive Exosome Population (LCMA) from Phosphatidylserine-Negative Exosomes A cationic metal affinity monolith (TREN) is loaded with ferric iron, then equilibrated with CV of 50 mM Tris, 20 mM NaCl, pH 7.5. Filtered mammalian cell culture harvest containing a mixture of phosphatidylserine-positive exosomes and phosphatidylserine-negative exosomes is applied to the column. Unbound sample components are rinsed from the column. Phosphatidylserine-positive exosomes are removed by a washing step with 50 mM Tris, 1.0 M sodium chloride, pH 7.0, then continuing under those conditions for 5 CV. The column is optionally re-equilibrated to its original equilibration conditions. Phosphatidylserine-positive exosomes are recovered by eluting the column with 1 M potassium phosphate. The column is then cleaned with 1 M NaOH plus 2 M NaCl.

Example 4

Fractionation of a Desired Lipid-Enveloped Virus (LCMA) from Chromatin Heteroaggregates Including Degraded Remnants from LMCAs A cationic metal affinity monolith (TREN) is loaded with ferric iron, then equilibrated with 15 CV of 50 mM Tris, 20 mM NaCl, pH 7.5. Filtered mammalian cell culture harvest containing a mixture of coronavirus, chromatin, and heteroaggregates including chromatin and degraded LMCA remnants is loaded onto the column. Unbound sample components are rinsed from the column with equilibration buffer and the column is eluted by a 20 CV linear gradient to 50 mM Tris, 1.0 M sodium chloride, pH 7.0, then continuing under those conditions for 5 CV. The column is then cleaned with 1 M NaOH plus 2 M NaCl.

Example 5

Reduction of Chromatin in Advance of Performing the Method of the Invention for Purification of Exosomes Particles-bearing iminodiacetic acid charged with ferric iron are equilibrated to 20 mM Tris, 50 mM NaCl, pH 7.5. They are mixed with filtered cell culture harvest bearing exosomes and contaminants at a proportion of 5% particles and incubated by mixing for 2 hours. The particles are allowed to settle, and the supernatant is filtered through a 0.45 μm membrane filter. Removal of solids facilitates filtration of the supernatant to a degree that permits its concentration by a factor of 20-100 by tangential flow filtration (TFF) with membranes characterized by pores in the size range of 300 kDa to 750 kDa. During TFF, the buffer composition is changed to 20 mM Tris, 20 mM NaCl, pH 7.5, after which the sample is processed by the method of the invention as described in Example 2.

Example 6

Reduction of Chromatin in Advance of Performing the Method of the Invention for Purification of Exosomes Particles-bearing iminodiacetic acid charged with ferric iron are equilibrated to 20 mM Tris, 50 mM NaCl, pH 7.5.

They are mixed with filtered cell culture harvest bearing exosomes and contaminants at a proportion of 5% particles and incubated mixing for 2 hours. The particles are allowed to settle, and the supernatant is filtered through a 0.45 μm membrane filter. Removal of solids facilitates filtration of the supernatant to a degree that permits its concentration by a factor of 20-100 by tangential flow filtration (TFF) with membranes characterized by pores in the size range of 300 kDa to 750 kDa. During TFF, the buffer composition is changed to 20 mM Tris, 500 mM sodium chloride, 5 mM magnesium chloride, pH 7.5. The sample is treated with a salt-tolerant nuclease enzyme then TFF is recommenced to remove liberated nucleotides, histones, and excess magnesium ions while changing the buffer composition to 50 mM Tris, 20 mM sodium chloride, pH 7.5. The sample may be concentrated further during this step. The sample is processed by the method of the invention as described in Example 2.

Example 7

Reduction of Chromatin after Performing the Method of the Invention for Purification of Exosomes After performing the method of Example 5 or Example 6 and following with the method of the invention as described in Example 2, the sample is diluted or buffer exchanged to conditions approximating 50 mM Tris, 20 mM sodium chloride, pH 7.5. A strong anion exchange column is equilibrated to those conditions and the sample loaded. Exosomes are eluted from the column with a 20 CV linear gradient to 1 M NaCl. The column is then cleaned with 1 M NaOH. The additional processing step further reduces chromatin and other contaminant levels.

REFERENCES

All references cited herein are incorporated by reference to the full extent to which the incorporation is not inconsistent with the express teachings herein.

[1]K Vrabec, T Lojpur, P Gagnon, Emerging tools for exosome purification and in-process monitoring, Bioprocess International eBook, 5 22 Mar. 2019, bioprocessintl-.com/analytical/downstream-validation/emerging-tools-for-exosomepurification-and-in-process-monitoring

[2]P Gagnon, K Vrabec, T Lojpur, A Strancar, Setting a cornerstone for platform purification of exosomes, Bioprocess International 18 (2020) 28-51, bioprocessintl-.com/downstream-processing/separation-purification/setting-a-cornerstonefor-exosome-purification-platform

[3] P Gagnon, R Nian, J Lee, L Tan, SM Abdul-Latiff, CL Lim, C CHuah, X Bi, YS Yan, W Zhang, H T Gan, Nonspecific interactions of chromatin with immunoglobulin G and protein A, and their impact on purification performance, J Chromatogr A 1340 (2014) 68-78.

[4]S Staubach, P Gagnon, K Vrabec, T Lojpur, S Peljhan, B Giebel, A Strancar, Challenges in industrial process development of exosome-based therapies: characterizing and managing diversity, BioProcess International, 2020, bioprocessintl.com/analytical/downstreamdevelopment/classification-of-extracellular-vesicles-using-chromatography-for-exosometherapy-production

[5] R Sharma, X Huang, R Brekken, A Schoit, Detection of phosphatidylserine-positive exosomes for diagnosis of early-stage malignancies, Br J Cancer 117 (2017) 545-552.

The invention claimed is:

1. A chromatographic method for separation of lipid-membrane-enclosed compound assemblages (LMCAs) from chromatin heteroaggregates including degraded remnants from LMCAs in a sample comprising the steps of, contacting the sample with a chromatographic material with a surface having cationic metal affinity ligands said chromatographic material being charged with ferric iron, manganese, calcium, or magnesium ions, and being equilibrated with an equilibration buffer, and applying a gradient of a first elution buffer comprising a non-metal-chelating salt, thereby eluting LMCAs.

2. The method of claim 1, wherein the LMCA is selected from the group consisting of a cellular vesicle, an extra-cellular vesicle, a non-cellular vesicle, a cellular organelle, an exosome, a small extra-cellular vesicle, a microvesicle, a medium extra-cellular vesicle, a ribosome, a mitochondrion, a lipid-enveloped virus or lipid-enveloped virus-like particle, an influenza virus, a corona virus, a lentivirus, a cytomegalovirus, a liposome and combinations thereof.

3. The method of claim 1, wherein the non-metal-chelating salt is a monovalent halide salt.

4. The method of claim 1, wherein the sample is selected from the group consisting of a cell culture harvest, a filtered cell culture harvest, a concentrated filtered cell culture harvest and a partially purified preparation containing a LMCA and chromatin heteroaggregates including LMCA remnants.

5. The method of claim 1, wherein chromatin heteroaggregates that include degraded remnants from LMCAs are eluted in a gradient of a second eluting buffer comprising a chelating salt.

6. The method of claim 5, wherein the chelating salt of the second eluting buffer is selected from the group consisting of a metal phosphate salt, a metal citrate salt, a metal salt of ethylenediaminetetraacetic acid (EDTA), a metal salt of ethylene glycol-bis(3-aminoethyl ether)-N,N,N',N'-tetraacetic acid (EGTA) and combinations thereof.

7. The method of claim 1, wherein the method is combined with at least one additional method for reduction of chromatin heteroaggregate content.

8. The method of claim 7, wherein the at least one additional method is a treatment with a solid phase bearing an anionic chromatography ligand.

9. The method of claim 8, wherein the solid phase bearing an anionic chromatography ligand is charged with iron or manganese ions.

10. The method of claim 1, wherein the sample is contacted with the chromatographic material and after an incubating time separated from the chromatographic material.

11. The method of claim 8, wherein the sample contains exosomes and is diafiltered by tangential flow filtration.

12. The method of claim 1, wherein the cationic metal affinity ligand is tris(2-aminoethyl)amine (TREN).

13. The method of claim 1, wherein the equilibration buffer comprises a pH value in the range of pH 5 to pH 9.

14. The method of claim 1, wherein the equilibration buffer has a conductivity value in the range of 1 mS/cm to 250 mS/cm.

15. The method of claim 7, wherein the at least one additional method is a treatment with nuclease enzymes.

16. The method of claim 11, wherein the sample is a cell culture harvest.

17. The method of claim 1, wherein the non-metal-chelating salt is sodium chloride.

18. The method of claim 1, wherein the equilibration buffer comprises a pH value in the range of pH 6.5 to pH 7.5.

19. The method of claim 1, wherein the equilibration buffer has a conductivity value in the range of 5 mS/cm to 10 mS/cm.

* * * * *